United States Patent
Stafford et al.

(10) Patent No.: US 6,346,247 B1
(45) Date of Patent: Feb. 12, 2002

(54) PREVENTION AND TREATMENT OF AUTOIMMUNE DISEASE WITH LUMINALLY ADMINISTERED POLYCLONAL ANTIBODIES

(75) Inventors: Douglas C. Stafford; John A. Kink, both of Madison, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 09/429,511

(22) Filed: Oct. 28, 1999

(51) Int. Cl.$^7$ ............................................. A61K 39/395
(52) U.S. Cl. ................................ 424/158.1; 424/139.1; 424/804; 424/810; 530/861; 530/868
(58) Field of Search .......................... 514/12; 424/139.1, 424/158.1, 810, 804; 530/861, 868

(56) References Cited

U.S. PATENT DOCUMENTS

| | | | |
|---|---|---|---|
| 4,968,607 A | | 11/1990 | Dower et al. |
| 5,891,432 A | | 4/1999 | Hoo |
| 5,891,679 A | | 4/1999 | Lucas et al. |
| 5,892,003 A | | 4/1999 | Davis et al. |
| 5,902,584 A | | 5/1999 | Nicholson et al. |
| 5,919,452 A | * | 7/1999 | Le et al. |
| 5,919,456 A | | 7/1999 | Puri et al. |
| 5,919,903 A | | 7/1999 | Gubler et al. |
| 5,922,573 A | | 7/1999 | Bossu et al. |
| 5,925,351 A | | 7/1999 | Browning et al. |
| 5,925,735 A | | 7/1999 | Baumgartner et al. |
| 5,932,704 A | | 8/1999 | Jubinsky |
| 5,939,063 A | | 8/1999 | Vadas et al. |
| 5,945,310 A | | 8/1999 | Young et al. |
| 5,945,397 A | | 8/1999 | Smith et al. |
| 5,945,511 A | | 9/1999 | Lok et al. |
| 5,955,290 A | | 9/1999 | Stahl et al. |
| 5,955,291 A | | 9/1999 | Alitalo et al. |
| 5,955,303 A | | 9/1999 | Au-Young et al. |
| 5,958,442 A | | 9/1999 | Wallace et al. |
| 5,959,085 A | | 9/1999 | Garrone et al. |
| 5,965,132 A | | 10/1999 | Thorpe et al. |
| 5,965,697 A | | 10/1999 | Czaplewski et al. |
| 5,965,704 A | | 10/1999 | Lok et al. |
| 5,968,524 A | | 10/1999 | Watson et al. |
| 5,969,105 A | | 10/1999 | Feng et al. |

FOREIGN PATENT DOCUMENTS

| EP | 0 695 189 B | * | 2/1996 |
|---|---|---|---|
| WO | WO 95/24918 | * | 9/1995 |

OTHER PUBLICATIONS

Paul, Fundamental Immunology, Fourth Edition, Lippincott Raven, Pa., p. 1083, 1999.*
Feldman et al., Cytokines in Autoimmunity, edited by Brennan and Feldman, Landes Co. U.S. pp. 1–23, 1996.*
Elliot et al. Cytokines in Immunity, edited by Brennan and Feldman, Landes CO. US, pp. 239–256, 1996.*
Fox J. Amer. Med. 99:81–88, 1995.*
Brennan and Feldman, Cytokines in Immunity, edited by Brennan and Feldman, Landes Co., US., pp. 25–47, 1996.*
Janeway et al Immunolbiology, Third edition, Current Biology Limited, NY, pp.12:30–31 and 13:11 and G:20, 1997.*
Polson et al., "Antibodies to Proteins from yolk of Immunized Hens," *Immunol. Comm.*, 9:495–514 (1980).
J. Rothe et al., "Mice lacking the tumour necrosis factor receptor 1 are resistant to TNF–mediated toxicity but highly susceptible to infection by *Listeria monocytogenes*," *Nature*, 364:798–802 (1993).
C.J. Boitard et al., "Pathogenesis of IDDM: Immune Regulation and Induction of Immune Tolerance in the Nod Mouse," *Autoimmunity* 15 (Suppl):12–13 (1993).
A.A. Rossini et al., "Immunology of Insulin–Dependent Diabetes Mellitus," *Annu. Rev. Immunol.*, 3:289–320 (1995).
A.N. Theofilopoulos and F.J. Dixon, "Murine Models of Systemic Lupus Erythematosus," *Adv. Immunol.*, 37:269–390 (1985).
Haworth,C. et al., "Cytokine and Anti–Cytokine Therapy," *The Cytokine Handbook*, 3rd Ed., A. Thomson ed. Chapter 28 (1998 p. 777–802.
Geoffrey, R., "Cytokines and their Receptors as Potential Therapeutic Targets," *The Cytokine Handbook*, 3rd Ed., A. Thomson ed., Chapter 32 (1998) p. 885–952.
Weigle WO., "Advances in basic concepts of autoimmune disease," *Clinics in Laboratory Medicine*, 17:329–340 (1997).
Karussis DM. et al., "Immunomodulating therapeutic approaches for multiple sclerosis," *J of Neurological Sciences* 153:239–250 (1998).
Godiska R. et al., "Chemokine expression in murine experimental allergic encephalomyelitis," *J. of Neuroimmunology* 58:167–176 (1995).
Brennen FM. et al., "Cytokines in autoimmunity," *Current Opinion in Immunology*, 8: 872–877 (1996).
The Lenercept Multiple Sclerosis Study Group. "TNF neutralization in MS: Results of a randomized, placebo–controlled multicenter study," *Neurology* 53:457–465 (1999).
Kassiotis G et al., "TNF accelerates the onset but does not alter the incidence and severity of myelin basic protein–induced experimental autoimmune encephalomyelitis," *Eur. J. Immunol.* 29:774–780 (1999).

(List continued on next page.)

Primary Examiner—David Saunders
Assistant Examiner—Amy DeCloux
(74) Attorney, Agent, or Firm—Medlen & Carroll, LLP

(57) ABSTRACT

The prevention and treatment of autoimmune disease in humans (as well as other animals) is described through the use of ligands directed to cytokines. Antibodies and receptors to the proinflammatory cytokines IL-2, TNF, IL-12 and IFN-gamma are employed (along with other ligands to such cytokines). Such ligands administered luminally are effective (as demonstrated in two experimental models of autoimmune disease) at delaying the onset of autoimune disease.

18 Claims, No Drawings

OTHER PUBLICATIONS

Rothe H. et al., "Interleukin–12 gene expression is associated with rapid development o diabetes mellitus in non–obese diabetic mice," *Diabetolgia* 39:119–122 (1996).
Frei K. et al., "Tumor necrosis factor and lymphotoxin–α are not required for induction of acute experimental autoimmune encephalolnyelitis", *J. Exp. Med.* 185:2177–2182 (1997).
Steinman L., "Some misconceptions about understanding autoimmunity through experiments with knockouts," *J. Exp. Med.* 185:2039–2041 (1997).
Kroemer G. et al., "The role of interleukin 2 in autoimmunity," *Immunology Today* pp. 246–251 (1989).
Hasko G et al., "IL–12 as a therapeutic target for pharmacological modulation in immune– and inflammatory diseases: regulation of T helper 1/ T helper 2 responses," *Br J Pharmacol* 127:1295–1304 (1999).
Fox DA., "Biological therapies: A novel approach to the treatment of autoimmune disease," *Ameican J. Medicine* 99:82–88 (1995).
Karges W. et al. "Immunological aspects of nutritional diabetes prevention in the NOD mice," *Diabetes* 46:557–564 (1997).
Persson, S et al., "Interleukin–10 suppresses the development of collagen type II–induced arthritis and ameliorates sustained arthritis in rats," *Scand. J. Immunol.* 44:607–614 (1996).
Zheng XX et al., "IL–2 receptor–targeted cytolytic IL–2/Fc fusion protein treatment blocks diabetogenic autoimmunity in nonobese diabetic mice," *J. of Immunology* 163:4041–4048 (1999).
Weiner HL., "Oral tolerance: immune mechanisms and treatment of autoimmune diseases," *Immunology Today* 18;335–343 (1997).
Miller, A et al., "Orally administered myelin basic protein in neonates primes for immune responses and enhances experimental autoimmune encephalomyelitis in adult animals," *Eur. J. Immunol.*, 24:1026–1032 91994).
Soos TM. et al., "Oral feeding of interferon tao (IFN)can prevent the acute and Chronic relapsing forms of experimental allergic encephalomyelitis," *J. Neuroimmunology* 75:43–50 (1997).

Elliot EA et al., "Immune tolerance mediated by recombinant proteolipid protein prevents experimental autoimmune encephalomyelitis," *J. of Neuroimmunol* 79:1–11 (1997).
Choy, EHS. et al., "Monoclonal antibody therapy in rheumatoid arthritis," *British Rheumatology* 37:484–490 (1998).
Achiron A. et al., "Intravenous immunoglobulin treatment in multiple sclerosis," *Neurology* 50:398–402 (1998).
Banerjee S. et al., "Immunosuppression of collagen–induced arthritis in mice with an anti–IL–2 receptor antibody," *J of Immunology* 141:1150–1154 (1988).
Lenschow DJ. et al., "Differential effects of anti–B7–1 and anti–B7–2 monoclonal antibody treatment on the development of diabetes in the nonobese diabetic mouse," *J. Exp. Med.* 181:1145–1155 (1995).
Kelley VE. et al., "Anti–interleukin 2 receptor antibody suppresses murine diabetic insulitis and lupus nephritis," *J. of Immunology* 140:59–61 (1988).
Wofsy D, et al, "Reversal of advanced murine lupus in mice by treament with monoclonal antibody to L3T4," *J of Immunol* 138:3247–3253 (1987).
Williams RO. et al., "Anti–tumor necrosis factor ameliorates joint disease in murine collagen–induced arthritis," *PNAS* 89:9784–9788 (1992).
Ruddle NH. et al., "An antibody to lymphotoxin and tumor necrosis factor prevents transfer of experimental allergic encephalomyelitis," *J. Exp. Med.* 172:1193–1200 (1990).
Butler DM. et al., "Anti–IL–12 and anti–TNF antibodies synergistically suppress the progression of murine collagen–induced arthritis," *Eur. J. Immunol.*, 29:2205–2212 (1999).
Ishida H. et al., "Continuous administration of anti–interleukin 10 antibodies delays onset of autoimmunity in NZB/ WF1 mice," *J. Exp. Med.* 179:305–310 (1994).
Leonard JP et al., "Prevention of experimental autoimmune encephalomyelitis by antibodies against interleukin 12," *J. Exp. Med* 181:381–386 (1995).
Heremans H. et al. Chronic relapsing experimental autoimmune encephalomyelitis (CREAE) in mice: enhancement by monoclonal antibodies against interferon–γ (gamma), *Eur. J. Immunol.* 26:2393–2398 (1996).

* cited by examiner

PREVENTION AND TREATMENT OF AUTOIMMUNE DISEASE WITH LUMINALLY ADMINISTERED POLYCLONAL ANTIBODIES

FIELD OF THE INVENTION

The present invention relates to therapeutics for the prevention and treatment of autoimmune disease, and in particular the prevention and treatment of autoimmune disease in humans through the use of luminally administered polyclonal antibody.

autoreactivity is largely directed toward a broad range of antigens and involves a number of tissues. Disease in either type results from the generation of one or both autoreactive cell types (B or T cells). Autoreactive B cells leads to the generation of autoantibodies or immune complexes. Autoreactive T cells leads to the cellular DTH responses from $T_{DTh}$ cells or cytotoxic responses from $T_C$ cells. Some autoimmune diseases in humans and the immune response and antigen(s) involved are shown in Table 1.

TABLE 1

Human Autoimmune Diseases

| Disease | Self-Antigen | Immune Response |
|---|---|---|
| Organ-Specific Autoimmune Disease | | |
| Addison's disease | Adrenal cells | Autoantibodies |
| Autoimmune hemolytic anemia | Red blood cells | Autoantibodies |
| Goodpasture's disease | Renal and lung membranes | Autoantibodies |
| Graves' disease | Thyroid-stimulating hormone receptor | Autoantibodies |
| Hashimoto's thyroiditis | Thyroid proteins | $T_{DTH}$ cells, autoantibodies |
| Idiopathic thrombocytopenia | Platelet membranes | Autoantibodies |
| Insulin-dependent diabetes mellitus (IDDM) | Pancreatic beta cells | $T_{DTH}$ cells, autoantibodies |
| Myasthenia gravis | Acetylcholine receptors | Autoantibodies |
| Myocardial infarction | Heart muscle | Autoantibodies |
| Pernicious anemia | Gastric intrinsic factor | Autoantibodies |
| Poststreptococcal glomerulonephritis | Kidney | Immune complexes |
| Spontaneous infertility | Sperm | Autoantibodies |
| Systemic Autoimmune Disease | | |
| Ankylosing spondylitis | Vertebrae | Immune complexes |
| Multiple sclerosis | Brain or white matter | $T_{DTH}$ and $T_c$ cells, autoantibodies |
| Rheumatoid arthritis | Connective tissue | Autoantibodies, immune complexes |
| Scleroderma | Nuclei, heart, lungs, GI tract, kidney | Autoantibodies |
| Sjogren's syndrome | Salivary gland, liver, kidney, thyroid | Autoantibodies |
| Systemic lupus erythematosus (SLE) | DNA, nuclear protein, RBC and platelet membranes | Autoantibodies, immune complexes |

BACKGROUND OF THE INVENTION

A progressive and maintained response by the immune system against self-components is termed autoimmunity. Normally self-tolerance mechanisms prevent the immune response from acting on self-components. However, all mechanisms have a risk of breakdown and occasionally the immune system turns on its host environment in an aggressive manner as to cause disease. This breakdown leads to the copious production of autoreactive B cells producing autoantibodies and/or autoreactive T cells leading to destructive autoimmune disease. The cellular mechanisms of autoimunity are the same as those involved in beneficial immune responses to foreign components which include antibody-dependent cell cytotoxicity, delayed-type hypersensitivity (DTH), and T-cell lympholysis.

Human autoimmune diseases can be divided into two categories: organ-specific and systemic. In organ-specific autoimmune disease, autoreactivity is directed to antigens unique to a single organ. In systemic autoimmune disease, The current view of the etiology of autoimmune diseases posulates that both autoreactive T and B cells exist normally in the body. Control of these cells involves immune surveillance mechanisms which can induce tolerance to these cells and/or the selective elimination of these cells. Factors which overcome immune surveillance are thought to be responsible for the proliferation of these autoreactive cells leading to autoimmune disease.

Immune surveillance can be circumvented in several proposed ways: (1) Autoreactive cells can be stimulated through molecular mimicry by cross-reactive microbial antigens. A number of viruses and bacteria have been shown to possess antigenic determinants that are identical to normal host-cell components. Thus, antibodies generated against these microbial antigens can also recognize and damage host cells. Cross-reacting antibodies to heart muscle developed after a Streptococcus infection, for example, is thought of be the cause of an rheumatic fever. (2) In some cases, foreign antigen can directly stimulate autoreactive cells. Lipopolysaccharides or viral antigens from Epstein-Barr virus (EBV) or cytomegalovirus causes the direct stimulation of certain B cells. During mononucleosis, a disease caused by EBV, a variety of autoantibodies reactive to self-components are generated. Specifically, EBV can activate B cells to produce autoantibodies to nuclear DNA and immune cells. (3) Release of antigens normally sequestered from the immune system is another example of the breakdown of immune surveillance leading to autoimmune disease. Experimentally, animals injected parenterally with basic myelin protein, an antigen primarily found in the brain, develop experimental autoimmune encephalomyelitis. (4) Expression of specific HLA alleles has been associated with autoimmune individuals. It is thought that cells expressing these HLA's may act as a prime target for autoreactive cells. Individuals with the B27 HLA allele has a 90% increased relative risk of developing ankyosing spondylitis.

Current therapies for autoimmune diseases are not cures, but are aimed at reducing symptoms to provide the patient with a acceptable quality of life. In organ-specific autoimmune disorders, the symptoms can be corrected by the removal of the organ if possible. In some autoimmune diseases such as myasthenia gravis some success have been achieved by removing the thymus. In addition, in organ-specific autoimmune disorders, symptoms can be corrected by metabolic control with biologically active compounds. For example, hypothroidism can be controlled by the administration of thryroxine or perrrnicious anemia can be treated with injections of vitamin $B_{12}$. Drugs used in most cases of autoimmune disease, especially systemic autoimmune disease, provide general nonspecific suppression of the immune system. For the most part these drugs do not distinguish between the pathological immune response and the protective immune response. Immunosuppressive drugs (e.g., corticosteroids, azathioprine, cyclophoshamide and cyclosporin) are often given to suppress the proliferation of autoreactive lymphocytes. Anti-inflammatory drugs also are prescribed to patients with rheumatoid arthritis. Unfortunately these drugs, besides not working in many patients, have very serious side-effects. The general suppression of the immune response puts the patient at greater risk to infection and cancer.

Clearly there is a significant need for agents capable of preventing and treating autoimmune diseases. It would be desirable if such therapy could be administered in a cost-effective and timely fashion, with a minimum of adverse side effects.

SUMMARY OF THE INVENTION

The present invention relates to therapeutics for the prevention and treatment of autoimmune disease. Specifically, the present invention contemplates the prevention and treatment of autoimmune disease in humans as well as other animals through the use of ligands directed to cytokines. The examples of the present invention demonstrate the production of antibodies to the proinflammatory cytokines IL-2, TNF, IL-12 and IFN-gamma (although other ligands to such cytokines are also contemplated). The examples of the present invention demonstrate a novel finding that ligands (such as antibodies) against pro-inflammatory cytokines such IL-2 or IL-12 administered orally are effective (as demonstrated in two experimental models of autoimmune disease) at delaying the onset of autoimune disease.

In one embodiment, the present invention contemplates a method of treatment, comprising: a) providing: i) a human patient who is either at risk for autoimmune disease or who has symptoms of autoimmune disease, ii) a therapeutic formulation comprising one or more ligands directed to a proinflammatory cytokine, and; b) administering said formulation to said patient. It is not intended that the present invention be limited to the type of patient. In one embodiment, the patient is a child.

The present invention is also not limited by the degree of benefit achieved by the administration of the anti-cytokine ligands. For example, the present invention is not limited to circumstances where all symptoms are eliminated. In one embodiment, said administering reduces said symptoms (e.g., the amount of autoantibody is reduced and/or the amount of pain is reduced). In another embodiment, said administering delays the onset of symptoms.

It is not intended that the present invention be limited by the route of administration. In one embodiment, the formulation is administered to the lumen of the intestine. In a preferred embodiment, said administering is performed orally. However, said administering can also be performed parenterally.

Where antibodies are the ligand employed, the present invention is not limited to the source of the anti-cytokine antibodies. In one embodiment, said antibodies are avian polyclonal antibodies (including but not limited to chicken antibodies). In one embodiment, said antibodies are purified antibodies. In the case of chicken antibodies, it is convenient that said chicken antibodies are purified from chicken eggs.

In accordance with the present invention, one or more members from the class of IL receptors or IL receptor analogues are selectively employed in soluble form to treat autoimmune patients. The present invention also contemplates using soluble tumor necrosis factor (TNF) receptors, or TNF receptor analogues, to treat autoimmune patients. In another embodiment, the method comprises treating with a therapeutic preparation comprising, in combination, both soluble TNF and soluble IL receptors.

The existence of membrane receptors to cytokines is now well-established. Many of these receptors have now been cloned and expressed in high yield. See U.S. Pats. Nos. 4,968,607, 5,925,351, 5,919,903, 5,919,456, 5,965,704, 5,945,511, 5,945,397, 5,925,735, all of which are hereby incorporated by reference.

DESCRIPTION OF THE INVENTION

The present invention contemplates the use of ligands (e.g., receptors, receptor fragments, antibodies and antibody fragments) directed to proinflammatory cytokines and inflammatory mediators administered to or at the lumen to treat autoimmune diseases. In one embodiment antibodies (raised in birds or mammals) against the offending inflammatory mediators are contemplated and these antibodies can be administered systemically, orally or mucosally either prophylatically or therapeutically to the patient. A variety of classes of inflammatory mediators are contemplated to be important to generate antibodies useful in the prevention and treatment of inflammatory diseases. Illustrative cytokines and inflammatory mediators are shown in Table 2. It is envisioned that ligands against these mediators would be used either singly or in combination to treat a specific disease. Combination therapies would consist of ligands to several mediators within a given pathway.

It is not intended that the present invention be limited to a particular mechanism. Indeed, and understanding of the precise mechanism by which the administration of ligands to cytokines achieves a therapeutic benefit is not necessary in order to successfully practice the present invention. While not limited to any particular mechanism, the inventors believe that cytokines play a major role in the initiation and regulation in immune responses and that the dysregulation of the cytokine network may also lead to the activation of autoreactive T cells leading to autoimmune. Preferential activation of a specific set of T cells, $T_H1$, is thought to play a central role in the pathogenesis of a number of autoimmune diseases. T cells with the CD4 phenotype are divided into subsets referred as $T_H1$ and $T_H2$ based on the nature of their immune reactivity and their cytokine secretion profile. $T_H1$ cells are associated cell-mediated inflammatory reactions and act as effector cells in infectious disease. Secreted cytokines that set the $T_H1$ subset apart are interferon gamma, tumor necrosis factor (TNF) interleulin-2 (IL-2) and upon activation interleukin-12 (IL-12). $T_H1$ cytokines are referred to as proinflammatory cytokines because they activate cytotoxic, inflammatory and delayed hypersensitiviy reactions. In contrast, $T_H2$ cells are associated with helper cell finction and antibody production. $T_H2$ cells upon activation secrete interleukins 4 (IL-4), 5 (IL-5), and 10 (IL-10). Cytokines from a $T_H1$ cells tend to inhibit the actions of the $T_H2$ cell and vice versa. Whether the characterization of such cells is correct or not, the data shows that the therapeutic methods (described in more detail below) result in a dramatic delay and/or reduction in autoimmune symptoms and disease.

Such delivery can be achieved by a variety of routes (e.g., oral, rectal, etc.) in a variety of vehicles (e.g., tablet, suppository, etc.). By contrast, a parenteral administeration is not designed to preferentially deliver compounds to the lumen (although some incidental delivery can take place through normal biodistribution).

The phrase "symptoms of autoimmune disease" is herein defined as any abnormal symptoms than can be attributed to the generation of autoreactive B and/or T cells. For example, autoantibodies are a common symptom associated with autoimmune disease.

The phrase "at risk for autoimmune disease" is herein defined as individuals with familial incidence of autoimmunity. For example, many autoimmune diseases are associated with genetic factors such as certain HLA specificities.

A "proinflammatory cytokine" is any cytokine that can activate cytotoxic, inflammatory or delayed hypersensitivity reactions. Examples of such cytokines are IL-2, TNF and INF-gamma. Examples of inflammatory mediators are found in Table 2.

TABLE 2

Examples Of Inflammatory Mediators

| Class of Mediator | Specific Name |
| --- | --- |
| Colony Stimulating Factors (CSF) | Granulocyte-Macrophage CSF, Macrophage Growth Factor (Mp-CSF), Granulocyte CSF, Erythropoietin |
| Transforming Growth Factor (TGF) | TGF beta 1, 2, and 3 |
| Interferons (IFN) | IFN alpha, beta, gamma |
| Interleukins (IL) | IL-1, IL-2, IL-3, IL-6, IL-7, IL-9, IL-11, IL-12, IL-15 |
| Tumor Necrosis Factor (TNF) | TNF- alpha, beta |
| Adherence proteins | Intercellular Adhesion Molecule (ICAM), selections L, E, and P, Vascular Cell Adhesion Molecule (VCAM) |
| Growth Factor | Leukemia Inhibitory Factor (LIF), Macrophage Migration-Inhibiting Factor (MIF), Epidermal Growth Factor (EGF), Platelet-derived Growth Factor (PDGF), Fibroblast Growth Factor (FGF), Insulin-like Growth Factor (ILGF), Nerve Growth Factor (NGF), B-cell growth Factor (BCGF) |
| Chemokines | Monocyte chemoattractant proteins (MCP) -1, 2, and 3, Rantes, Macrophage Inflammatory Protein (MIP), IL-8, Growth-Related Oncogene (GRO-alpha), Gamma interferon-inducible protein (IP 10) |
| Leukotrienes (LTB) | Leukotriene $B_4$, Leukotriene $D_4$ |
| Vasoactive Factors | histamine, bradykinin, platelet activating factor (PAF) |
| Prostaglandins (PG) | $PGE_2$ |

DEFINTIONS

The phrase "ligand directed to a cytokine" is herein defined as meaning any molecule having affinity for a cytokine. Ligands can be chemically synthesized or designed by molecular evolution. Alternatively, such ligands can be known biomolecules or portions thereof (e.g., receptors, antibodies). It is not intended that the present invention be limited to the mechanism by which ligands achieve a therapeutic benefit. Ligands may be "antagonists" in that they neutralize the biological impact of a secreted cytokine. On the other hand, ligands may simply block recognition of cytokines or interfere with cell function. For example, ligands may interact with a cell-surface cytokine so as to result in immune cells not participating in autoimmune phenomenon (e.g., the cells are caused to enter apoptosis, etc.).

The phrase "administered to or at the lumen" is herein defined as administration that preferentially delivers compound(s) to the space in the interior of the intestines at a concentration in excess of what is found in circulation.

EXPERIMENTAL

The following examples serve to illustrate certain preferred embodiments and aspects of the present invention and are not to be construed as limiting the scope thereof.

EXAMPLE 1

Production Of Antibodies Proinflammatory Cytokines To IL-2, IL-12, TNF And IFN-Gamma In The Hen This example involved: (a) preparation of the immunogen and immunization, (b) purification of anti-IL-2, IL-12, TNF, and IFN-gamma chicken antibodies from egg yolk (IgY), and (c) detection of specific antibodies in the purified IgY preparations.

(a) Preparation Of The Immunogen And Immunization. Recombinant human (rH) Tumor Necrosis Factor Alpha, (TNF), recombinant mouse Interleukin 2, (IL-2), recombinant mouse Interferon-gamma, and recombinant mouse Interleukin 12 (heterodimer) was purchased (lyophilized without bovine serum albumin (BSA) and designated carrier-free) from R&D Systems Inc., Minneapolis, Minn. and produced in *E. coli*. The lyophilized cytokines were reconstituted in phosphate-buffered saline pH 7.2–7.5 (PBS) at least 50 ug/ml. From approximately 2 to 50 ug of each cytokine was used to immunize groups of hens. Each hen received one 0.5 ml sub-cutaneous injection containing the individual cytokine with 75 ug Quil A adjuvant (Superfos Biosector, Denmark, distributed by Accurate Chem., Westbury, N.Y.) in PBS. The hens were immunized every 2 weeks for at least 3 times then placed on a maintenance immunization schedule where the hens were immunized every 4–6 weeks.

(b) Purification Of Anti-Cytokine Chicken Antibodies From Egg Yolk (IgY). Groups of eggs were collected per immunization group at least 3–5 days after the last booster immunization. The chicken yolk immunoglobulin (IgY) was extracted by a two-step polyethylene glycol (PEG) 8000 method performed according to a modification of the procedure of Polson et al, *Immunol. Comm.*, 9:495 (1980). The yolks were separated from the whites and the yolks were placed in a graduated cylinder. The pooled yolks were blended with 4 volumes of PBS and PEG was added to a concentration of 3.5%. When the PEG was dissolved, the protein and lipid precipitates that formed were pelleted by centrifugation at 9,000×g for 15 minutes. The supernatants were decanted and filtered through 4 layers of gauze to remove the floating particulates and a second PEG step was performed by adding PEG to a fmal concentration of 12% (the supematants were assumed to contain 3.5% PEG). After a second centrifugation, the supernatants were discarded and the IgY pellets were resuspended in PBS at approximately ⅙ the original yolk volume. IgYs extracted from the eggs of immunized hens are designated as "immune IgY," while IgYs extracted from the eggs of unimmunized hens is designated "preimmune IgY." The concentration of the fractionated IgY's were estimated by measuring the absorbance at 280nm (an optical density at 280 nm of 1.3 equals 1 mg of IgY/ml. The antibody concentrations were about 20–35 mg/ml.

(c) Detection Of Anti-Cytokine Antibodies In The Purified IgY Preparations. In order to determine if an anti-cytokine response was generated and to determine relative levels of the response, enzyme-linked immunosorbent assays (EIA) were performed. Briefly, ninety-six well Falcon Pro-bind micro-titer plates were coated overnight at 4° C. with 100 ul/well with different cytokines (TNF, IL-2, IL-12, IFN-gamma at 0.1–1.0 ug/ml PBS. The wells are then blocked with PBS containing 1% BSA and 0.05% Tween 20 and incubated for about 1 hour at 37° C. The blocking solution was removed and the immune or preimmune IgY was diluted in PBS containing BSA and the plates were incubated for 1 hour at 37° C. The plates were washed 3 times with PBS containing 0.05% Tween 20 and three times with PBS alone. Alkaline phosphatase-conjugated anti-chicken IgG was diluted 1:1000 in PBS containing 1% BSA and 0.05% Tween 20, added to the plates and incubated 1 hour at 37° C. The plates were washed as above and p-nitrophenyl phosphate at 1 mg/ml in 0.05 M $Na_2CO_3$, pH 9.5, 10 MM $MgCl_2$ was added. The plates were read in a Dynatech plate reader at 410 nm about 30 minutes after substrate addition. Good antibody titers (reciprocal of the highest immune IgY generating a signal about 3-fold higher than that of preimmune) >10,000 were generated against a four cytokines.

The level of antibody response in the hens against all the cytokines tested were very good. Given the low amounts of antigen used for immunization, indicates cytokines may be very immunogenic in the hens and the avian system appears to be a well-suited method to generate anti-mammalian cytokine antibodies.

EXAMPLE 2

Determination Of Anti-TNF IgY Neutralizing Ability In A Cell-Based Neutralization Assay This example involved the testing of the anti-TNF IgY neutralizing ability in a cell-based neutralization assay. Bioactivity of the anti-TNF IgY antibody was evaluated in the murine L929 cell based neutralization assay as previously described (N. Mathews et al., 1987, Lymphokines and Interferons). Briefly, murine L929 cells(ATCC, Rockville, Md.), sensitive to the cytotoxic effects of recombinant human TNF (rhTNF), were grown in sterile conditions with Ham's F12 and Dulbecco's Modified Eagles media (1:1 vol:vol ratio), containing 1.2 g/L sodium bicarbonate and 15 mM Hepes (Life Technologies,Gaithersburg, Md.) and supplemented with 10% fetal bovine serum (Life Technologies). Cells were harvested using trypsin:EDTA (Life Technologies), and $2\times10^4$ cells were dispensed into each well of a 96-well flat-bottomed plate (Costar) and incubated for 20 hours in a humidified chamber at 37° C. and 5% $CO_2$. A commercial anti-TNF antibody, Remicade (a humanized mouse monoclonal antibody to human TNF, Centocor, Malvern, Pa.) served as a positive control, and a preimmune antibody, served as a negative control.

The IgY's were serially diluted in PBS (Life Technologies) supplemented with 1% BSA (wt:vol)(Life Technologies) and 10 ug/ml actinomycin D (ICN, Costa Mesa, Calif.). To each well containing antibody, an equal volume of 1 ng/ml rhTNF (R&D Systems, Minneapolis, Minn.) was added, including controls which received only rhTNF or only PBS diluent. The plate was then incubated for 1 hour at 37° C. Finally, the antigen-antibody mixture was added to the cells and incubated for 20 hours at 37° C., 5% $CO_2$ in a humidified chamber. Cell viability was measured using the chromogenic Cell Titre 96 Proliferation Assay (Promega Corporation, Madison, Wis.) recording the optical density at 490 nm. The amount of anti-TNF that resulted in the prevention of cell death in 50% and 90% of the cells, termed neutralization dose 50 and 90 (ND50 and ND90) was calculated for each antibody. The results demonstrated that the anti-TNF IgY was effective at neutralizing TNF compared to preimmune IgY in the L929 cell-based assay. The ND50 and ND90 was determined to be approximately 70 ng/ml and 100 ng/ml, respectively.

EXAMPLE 3

Determination Of Anti-IL-2 IgY Neutralizing Ability In A Cell-Based Neutralization Assay This example involved the testing of the anti-IL-2 IgY neutralizing ability in a cell-based neutralization assay. The ability of anti-IL-2 IgY to neutralize the bioactivity of IL-2 was determined in a cell-based assay based on a protocol described in *Current Protocols in Immunology*, Vol. 1, Section 6.3.4, 1994. CTLL-2 cell line (ATCC) requiring rhIL-2 (R&D systems) as a growth factor at 4 ng/ml was grown in RPMI 1640 with 10% fetal calf serum at 37° C. at 5% $CO_2$. Avian anti-IL-2 IgY was diluted serially two-fold with culture media in a 96 well microtiter plate. Goat anti-rh IL-2 IgG (R&D Systems) and preimmune IgY at the same concentrations were also serial diluted and served as positive and negative controls, respectively. Recombinant human IL-2 at 0.2 ng/well was added and pre-incubated with antibody for 1 hour at 37° C. CTLL-2 cells at $10^4$/well was then added and incubated for 20 hours at 37° C., 5% $CO_2$ in a humidified chamber. Cell viability was measured using the chromogenic Cell Titre 96 Proliferation Assay (Promega Corporation, Madison, Wis.) recording the optical density at 490 nm. The results demonstrated that the anti-IL-2 IgY was effective at neutralizing rhTNF compared to preimmune IgY in the CTLL-2 cell-based assay. The ND 90 of anti-IL-2 IgY was approximately 500 ug/ml.

EXAMPLE 4

Determination Of Anti-IL-12 Neutralizing Ability In A Cell-based Neutralization Assay This example involved the testing of the anti-IL-12 IgY neutralizing ability in a cell-based neutralization assay. To measure the ability of anti-IL-12 IgY (generated to the heterodimer isoform) to neutralize the bioactivity of rhIL-12 heterodimer a cell-based assay was performed using peripheral blood mononuclear cells, (PBMC's). PBMC's were purified and activated according to the procedure in *Current Protocols in Immunology*, Vol. 1, Section 6.16, 1994. Various concentrations of the anti-IL-12 IgY (2,500 ug/ml-0.032 ug/ml) were incubated with rhIL-12 (R&D Systems) at 1ng/ml for 1 hour at 37° C. in a 96 well plate. All dilutions were performed in the assay medium which consisted of a 1:1 dilution of RPMI (Life Technologies) and Dulbecco's Modified Eagles Medium (Life Technologies) with L-arginine (Life Technologies)at 2.5 mg/ml, 10% D-glucose (Sigma), and 10% human serum (Irvine Scientific). As a positive control, a commercially available anti-IL-12 (R&D Systems) was used, and as a negative control, preimmune IgY antibodies were used. Following the preincubation, the PBMC's were added to the antigen-antibody mixture at a final concentration of $2\times10^5$ cells/ml and incubated for 48 hours at 37° C. with 5% $CO_2$. During the final two hours of the incubation, Cell Titre 96 Proliferation Assay (Promega Corporation) was added, and the optical density was read at 490 nm. The assay indicated that anti-IL-12 IgY could neutralize rh IL-12 compared to preimmune IgY with an $ND_{50}$ estimated at 0.47 mg/ml. (Data not shown).

EXAMPLE 5

Determination Of Anti-IFN-Gamma Neutralizing Ability In Vivo With A Mouse Endotoxin Model This example involved the testing of the anti-IFN-gamma IgY neutralizing ability in a mouse endotoxin shock model. A bacterial lipopolysaccaride (LPS) model of endotoxin shock described by J. Roth et al., Nature, 364:798–802, 1993, was used to determine if anti-IFN-gamma IgY possessed neutralizing antibodies to IFN-gamma. Antibodies neutralizing to proinflammatory cytokines such as TNF and IFN-gamma have been reported to be effective in this model (Roth et al.). Equal concentrations of either preimmune IgY or anti-IFN-gamma IgY were pretreated with 1.2 mg of LPS from Salmonella enteritidis (Sigma) and incubated for 1 hour at 37° C. This pretreatment mixture (pretreatment)was then administered intraperitoneally into 18–20 G C57BL/6 mice (Charles River). Survival after challenge with LPS indicated that the antibodies were neutralizing against the cytokine. Similar experiments were preformed by directly administering the LPS/antibody mixture into mice without preincubation (premix). Results are shown in Table 3. The results indicated that anti-IFN-gamma IgY could effectively neutralize endogenous IFN-gamma produced by the mouse compared to preimmune control IgY in the LPS -endotoxin shock model.

TABLE 3

| Treatment | # of Survivors/ # Tested | % Survival |
| --- | --- | --- |
| Preimmune IgY (pretreatment) | 1/11 | 9 |
| Anti-IFN-gamma IgY (pretreatment) | 3/3 | 100 |
| Preimmune IgY (premix) | 0/6 | 0 |
| Anti-IFN-gamma IgY (premix) | 8/9 | 88 |

EXAMPLE 6

Treatment With Oral Anti-Cytokine Therapy In An Animal Model Of Insulin-Dependant Diabetes Mellitus An autoimmune animal model of insulin-dependant diabetes mellitus (IDDM) was used to determine if luminally-administered anti-cytokine therapy may be effective at preventing or delaying the onset of disease. IDDM is an autoimmune disease that effects about 0.2% of the population causes the destruction of the insulin-producing (beta) islet cells in the pancreas. This destruction involves the presence of pancreatic autoimmune antibodies and leukocytic infiltration (insulitis) of the pancreatic islet cells. These events effectively lower the amount of normal insulin needed to maintain normal glucose metabolism resulting in diabetes. Nonobese diabetic (NOD) mice spontaneously develop autoimmune T-cell mediated IDDM. Diabetes in the NOD mouse is similar to human IDDM in both genetics and autoimmune pathogenesis (C. J. Boitard et al., Autoimmunity 15 (Suppl):12–13, 1993 and A. A. Rossini et al., Annu. Rev. Immunol., 3:289–320, 1995). This mouse strain has provided an important model for dissecting the pathogenesis of autoimmune diabetes in humans. NOD mice spontaneously develop insulitis between 2–4 weeks of age and progresses to diabetes 10–20 weeks later in about 80% of the female mice and 20% of the male mice. Severe IDDM ensues that results in excessive urine production containing high levels of glucose. With time, severe IDDM eventually results in a death in a most of the NOD mice.

This example involves: a) description of establishment of the NOD model and treatment, b) Methods and results to determine oral anti-cytokine efficacy on the delay of onset of glycosuria (high levels of glucose in the urine and c) prevention of mortality from disease.

a) The NOD Model And Treatment. Six week old (about 20 gram) female NOD mice were purchased (The Jackson Laboratory, Bar Harbor Me.) and maintained under specific pathogen free (SPF) conditions. The maintenance of the mice in SPF conditions was performed according to procedures described in *Current Protocols in Immunology*, (1997) 15.9.1–15.9.23 by Edward H. Leiter (John Wiley & Sons, Inc.). SPF conditions required the use of autoclaved cages and barrier protected isolator lids with autoclaved food and bedding. The drinking water was filtered and acidified to pH 2–3 with HCl to prevent the growth of Pseudomonas. Groups of NOD mice (7/group) were aseptically treated orally with antibodies to two proinflammatory mediators, IL-2 and IL-12. Treatment controls consisted of treating mice orally with either vehicle (0.1 M carbonate buffer pH 9.2–9.5) or preimmune IgY. The IgY's were diluted in 0.1 M carbonate buffer to minimize IgY hydrolysis in the stomach. Treatments were sterile filtered (0.4 0 before use. Approximately 0.2 mls of a 20–40 mg/ml (200–400 mg/kg/day) of IgY solution was orally administered using a 20 G, 3.5 cm long feeding needle (Popper & Sons, New Hyde, N.Y.). Treatments were administered orally once per day, five days (weekdays) a week. Mid-way through the study, one mouse in the vehicle-treated group and one from the anti-IL-12 treated group died from dosing unrelated to IDDM disease.

b) Efficacy: Delay Of Onset Of Glycosuria. The monitoring of the glycemic status began on shortly after arrival using reagent strips to semi-quantitatively measure urine glucose. Either Diastix (glucose) or Uristix (glucose and protein) reagent strips for urinalysis were used (Bayer Diagnostics, Elkhart, IN). The level of glycemia was determined calorimetrically from turquoise to dark brown with the strips representing glucose levels of 100, 250, 500, 1000, and 2000 mg of glucose/dl. Individual mice were placed in clean cages without bedding and a drop of urine was collected on the test area and read after 30 seconds. Mice are considered diabetic with glycosuria when urine glucose levels were >250 mg/dl. Treatment results are shown in Table 4. The results indicate that oral anti-cytokine therapy using both anti-IL-2 and anti-IL-12 IgY could delay the onset of diabetes in the NOD mouse model. The onset of glycosuria first appeared when the mice were approximately 14–15 weeks old after about 8 weeks of treatment. Glycosuria first appeared at the same time in some mice treated with vehicle, preimmune and anti-Il-12 IgY. Initial onset of glycosuria in the anti-IL-2 treated mice was delayed. During treatments from approximately week 11 to week 16, 67% and 43% of vehicle treated and preimmune treated mice were glycosuric. In contrast, only 14% and 17% of the anti-Il-2 and anti-IL-12 treated mice, respectively were glycosuric. After 16 weeks of treatment nearly all the mice in the vehicle treated (100%) and preimmune treated mice (83%) had diabetes. In contrast, roughly half of the anti-cytokine treated groups (42% for anti-IL-2 and 67% for anti-IL-12) were diabetic. Preimmune IgY treatment compared to vehicle treatment was found to have no therapeutic effect in terms of delay of diabetes. Results, however indicated that the onset of diabetes in NOD mice with was delayed approximately 6 weeks after treatment with oral anti-cytokine therapy.

c) Efficacy: Prevention Of Mortality From Disease. Results indicated that oral anti-cytokine therapy using anti-IL-2 and anti-IL-12 IgY prevented death due to the complications of diabetes in the NOD mice model (Table 5). The time of death in the mice during treatment was monitored and closely coincided with several weeks of high glucose levels in the blood (2000 mg/dl). Death from diabetes started in both in the vehicle and preimmune treated mice at 17 weeks of age after about 11 weeks of treatment. Sixty-seven % of vehicle treated and 57% of preimmune treated NOD mice were dead after 22 weeks of age. Significantly, none of the anti-IL-2 treated and only 17% anti-IL-12 treated were dead after 22 weeks (Table 5). The results showed that oral anti-IL-2 and anti-IL-12 therapy in NOD mice could prevent mortality from disease compared to the control treated mice.

EXAMPLE 7

Treatment With Oral Anti-Cytokine Therapy In An Animal Model Of Systemic Lupus Erythematosus An autoimmune animal model of Systemic Lupus Erythematosus (SLE) was used to determine if oral anti-cytokine therapy may be effective at preventing or delaying the onset of disease. SLE is a systemic autoimmune disease that usually appears in women from 20 and 40 years of age and is characterized by fever, weakness, joint pain, erythematous lesions, pleurisy and kidney disfunction. Affected individuals may produce autoantibodies to a vast array of self-components such as DNA, red blood cells, and platelets. Immune complexes of autoantibodies are formed which are deposited on blood vessels resulting in vasulitis and glomerulonephritis in the kidney. The New Zealand black x New Zealand white $F_1$ hybrid mouse (NZB/W$^1$) spontaneously develop severe autoimmune disease that closely resembles SLE in humans (A. N. Theofilopoulos and F. J. Dixon, Adv. Immunol., 37:269, 1985). This model in particular has been very useful in understanding the immunological defects involved in the development of SLE autoimmunity. NZB/W$^1$ mice develop immune complex-mediated glomerulonephritis, resulting in the excretion of high levels of protein in the urine and an anti-DNA IgG serum response. As true with SLE in humans, the incidence of autoimmunity in NZB/W$^1$ female mice is much higher than males. Mice eventually develop a fatal disease around 6–9 months in female animals.

This example involves a description of: a) the NZB model and treatment, b) methods and results to determine oral anti-cytokine efficacy on the delay of onset of proteinuria (high levels of protein in the urine, c) Reduction of an anti-double stranded (ds) DNA serum response and d) Prevention of mortality from disease.

a) The NZB/W$^1$ Model And Treatment. Six week old (about 20 gram) female NZB/W$^1$ mice were purchased (The Jackson Laboratory, Bar Harbor Me.) and maintained under normal non-SPF conditions according to the breeder. Groups of NZB/W$^1$ mice (7/group) were treated orally with anti-IL-2 IgY or anti-IL-12 IgY diluted in 0.1 M carbonate buffer pH 9.2–9.5. Treatment control mice were treated orally with either vehicle (0.1 M carbonate buffer pH 9.2–9.5) or preirnmune IgY. Approximately 0.2 mls of a 20–40 mg/ml (200–400 mg/kg/day) of IgY solution was orally administered using a 20 G, 3.5 cm long feeding needle (Popper & Sons, New Hyde, N.Y.). Treatments were administered orally once per day, five days (week days) a week.

b) Efficacy: The Delay Of Onset Of Proteinuria. The presence of proteinuria in the NZB/W$^1$ mice was detected using reagent strips to semi-quantitatively measure urine protein. Uristix (glucose and protein) reagent strips for urinalysis were used (Bayer Diagnostics, Elkhart, Ind.). The presence of measurable amounts of protein in the urine by the reagent strips is considered abnormal and indicative of disease. The level of proteinuria was determined calorimetrically from light green (negative-trace) to dark green with the strips measuring protein levels of 30, 100, 300, and >2000 mg of protein/dl of urine. Individual mice were placed in clean cages without bedding and a drop was collected on the test area and read after 30 seconds. Mice are considered to have proteinuria when urine protein levels were >30 mg/dl. Treatment results are shown in Table 6. The results indicate that oral anti-cytokine therapy with either anti-IL-2 and anti-IL-12 could delay the onset of diabetes in the NZB/W$^1$ mouse model. The onset of proteinuria first appeared in the preimmune and vehicle-treated mice approximately when the mice were 14 weeks old after about 7 weeks of treatment. During treatments from week 7 to week 28 the majority (71%–100%) of the vehicle-treated or Preimmune-treated mice had proteinuria (>30 mg/dl). Significantly, proteinuria in the NZB/W$^1$ mice treated orally with either anti-IL-2 and anti-IL-12 IgY was not detected until week 21 of treatment. After 28 weeks of treatment most of the vehicle-treated and preimmune treated mice were proteinuric (86% (6/7)). In contrast, at week 28 of treatment, only 29% (2/7) of the anti-IL-2 treated mice and 43% (3/7)

of the anti-IL-12 IgY treated mice were proteinuric. These results indicate that oral anti-cytokine therapy to IL-2 and IL-12 could effectively delay the onset of proteinuria in NZB/W[1] mice compared to the control treated mice.

c) Reduction Of An Anti-Double Stranded (ds) DNA Serum Response. The presence of an anti-ds DNA response which is pathognomonic for SLE was determined using a commercial enzyme immunoasssay (EIA) kit designed to measure specific autoantibodies against ds DNA in human serum. Blood samples were taken at various times during treatment from each NZB/W[1] mouse from the tail vein. Serum was then collected after the blood was allowed to clot. The microtiter EIA assay (Bindazyme Anti-ds DNA EIA kit, The Binding Site, Birmingham, England) was performed on the serum samples according to manufacturers instructions except instead of using the anti-human peroxidase conjugate, a sheep anti-mouse IgG peroxidase (The Binding Site) was used. The sheep anti-mouse IgG peroxidase conjugate was diluted 1/10,000 in the assay as recommended by the manufacturer. Internal assay controls were run and serum samples were tested in duplicate. Tetramethylbenzidine substrate was used and after 10 minutes the plates were read at 450 nm. The higher the absorbance value the test serum at 450 nm, the higher the anti-ds DNA response. The average absorbance with the standard error of the mean of each treatment group at various times is shown in Table 7. The results shown a similar increase in an anti-ds DNA serum response in both the vehicle and preimmune treated mice. This response is roughly reduced by half in the anti-IL-2 and anti-IL-12 treated NZB/W[1] mice throughout the treatment regimen. The anti-ds DNA serum response in the anti-cytokine treated mice is delayed approximately 11 weeks comparing the results from week 17 to week 28. Results indicated that oral anti-cytokine therapy using anti-IL-2 and anti-IL-12 IgY could effectively reduce the anti-ds DNA response in NZB/W[1] mice compared to the control treated mice.

d) Prevention Of Mortality From Disease. Results indicated that oral anti-cytokine therapy using anti-IL-2 and anti-IL-12 could delay mortality due to the complications of SLE in the NZB/W[1] mice model (Table 8). The time of death in the mice during treatment was monitored and closely coincided with high anti-ds DNA levels in the serum. Death began to occur in the vehicle and preimmune-treated NZB/W[1] mice at 26 weeks of age (20 weeks of treatment) matching previous reports on this model. At a week 36, 57% (4/7) of vehicle treated and 71% (5/7) of preimmune-treated mice died from disease. In contrast, none of the mice in the anti-IL-2 have died and all still appeared healthy. While 28% of the mice treated with anti-IL-12 died, onset was delayed (the first animal in this group died at week 32 and the second at week 36). The results showed that oral anti-IL-2 and anti-IL-12 therapy in NZB/W[1] mice could prevent mortality from disease compared to the control treated mice.

Those skilled in the art will know, or be able to ascertain upon review of the above, using no more than routine experimentation, many equivalents to the specific embodiments of the invention described herein. These and all other equivalents are intended to be encompassed by the following claims.

TABLE 4

Oral anti-cytokine therapy prevents the onset of prevents glucosuria In NOD mice

| | % Diabetic Mice | |
|---|---|---|
| Treatment Group | Day 75 | Day 115 |
| Vehicle | 67 | 83 |
| Pre-immune | 43 | 100 |
| Anti-IL-2 | 14 | 43 |
| Anti-IL-12 | 17 | 67 |

TABLE 5

Oral anti-cytokine therapy prevents the onset of mortality In NOD mice

| Treatment Group | % Mortality |
|---|---|
| Vehicle | 67 |
| Pre-immune | 57 |
| Anti-IL-2 | 0 |
| Anti-IL-12 | 17 |

TABLE 6

Oral anti-cytokine therapy prevents the onset of proteinuria in NZB/W mice

| | % Proteinuria > 30 mg/dl | |
|---|---|---|
| Treatment Group | Week 11 | Week 28 |
| Vehicle | 100 | 86 |
| Pre-immune | 100 | 86 |
| Anti-IL-2 | 0 | 28 |
| Anti-IL-12 | 0 | 43 |

TABLE 7

Oral anti-cytokine therapy reduces an Anti-ds DNA response in NZB/W mice

| Treatment Group | Week 7 | Week 13 | Week 17 | Week 24 | Week 28 |
|---|---|---|---|---|---|
| | Average Absorbance .450 nm +/- SEM | | | | |
| Vehicle | 0.224 +/- 0.04 | 0.612 +/- 0.23 | 0.73 +/- 0.19 | 0.836 +/- 0.17 | 1.1 +/- 0.12 |
| Pre-immune | 0.225 +/- 0.09 | 0.693 +/- 0.26 | 0.75 +/- 0.14 | 0.855 +/- 0.1 | 1.17 +/- 0.03 |
| Anti-IL-2 | 0.158 +/- 0.02 | 0.236 +/- 0.06 | 0.384 +/- 0.32 | 0.494 +/- 0.13 | 0.577 +/- 0.14 |
| Anti-IL-12 | 0.116 +/- 0.01 | 0.130 +/- 0.01 | 0.388 +/- 0.2 | 0.633 +/- 0.18 | 0.814 +/- 0.16 |

TABLE 8

Oral anti-cytokine therapy prevents the onset of mortality in NZB/W mice

| Treatment Group | % Cumulative Mortality |
|---|---|
| Vehicle | 57 |
| Pre-immune | 71 |
| Anti-IL-2 | 0 |
| Anti-IL-12 | 28 |

What is claimed is:

1. A method of treatment, comprising:
   a) providing:
      i) a human patient with symptoms of autoimmune disease, wherein said autoimmune disease is selected from the group consisting of insulin-dependant diabetes mellitus and lupus erythematosus;
      ii) a therapeutic formulation comprising polyclonal antibody directed to a proinflammatory cytokine, wherein said cytokine is selected from the group consisting of IL-2 and IL-12; and
   b) orally administering said formulation to said patient.

2. The method of claim 1, wherein said administering reduces said symptoms.

3. The method of claim 1, wherein said antibody is avian polyclonal antibody.

4. The method of claim 3, wherein said avian antibody is purified antibody.

5. The method of claim 4, wherein said antibody is purified from eggs.

6. A method of treatment, comprising:
   a) providing:
      i) a human patient at risk of autoimmune disease, wherein said autoimmune disease is selected from the group consisting of insulin-dependant diabetes mellitus and lupus erythematosus;
      ii) a therapeutic formulation comprising polyclonal antibody directed to a proinflammatory cytokine, wherein said cytokine is selected from the group consisting of IL-2 and IL-12; and
   b) orally administering said formulation to said patient.

7. The method of claim 6, wherein said administering delays the onset of autoimmune symptoms.

8. The method of claim 6, wherein said antibody is avian polyclonal antibody.

9. The method of claim 8, wherein said avian antibody is purified antibody.

10. The method of claim 9, wherein said antibody is purified from eggs.

11. A method of treatment, comprising:
    a) providing:
       i) a human patient with symptoms of autoimmune disease, wherein said autoimmune disease is selected from the group consisting of insulin-dependant diabetes mellitus and lupus erythematosus;
       ii) a therapeutic formulation comprising avian polyclonal antibody directed to a proinflammatory cytokine, wherein said cytokine is selected from the group consisting of IL-2 and IL-12; and
    b) administering said formulation orally, thereby delivering said antibody to the lumen of the intestines of said patient.

12. The method of claim 11, wherein said administering reduces said symptoms.

13. The method of claim 11, wherein said avian antibody is purified antibody.

14. The method of claim 13, wherein said antibody is purified from eggs.

15. A method of treatment, comprising:
    a) providing:
       i) a human patient at risk of autoimmune disease, wherein said autoimmune disease is selected from the group consisting of insulin-dependant diabetes mellitus and lupus erythematosus;
       ii) a therapeutic formulation comprising avian polyclonal antibody directed to a proinflammatory cytokine, wherein said cytokine is selected from the group consisting of IL-2 and IL-12; and
    b) administering said formulation orally, thereby delivering said antibody to the lumen of the intestines of said patient.

16. The method of claim 15, wherein said administering delays the onset of autoimmune symptoms.

17. The method of claim 15, wherein said avian antibody is purified antibody.

18. The method of claim 17, wherein said antibody is purified from eggs.

* * * * *